United States Patent [19]

Hardtmann et al.

[11] 4,053,600

[45] Oct. 11, 1977

[54] TRICYCLIC 1,2,4-TRIAZOLO-QUINAZOLINES

[75] Inventors: Goetz E. Hardtmann, Morristown; Faizulla G. Kathawala, West Orange, both of N.J.

[73] Assignee: Sandoz, Inc., E. Hanover, N.J.

[21] Appl. No.: 590,041

[22] Filed: June 25, 1975

Related U.S. Application Data

[63] Continuation-in-part of Ser. No. 339,177, March 8, 1973, abandoned, which is a continuation-in-part of Ser. No. 209,425, Dec. 17, 1971, abandoned, which is a continuation-in-part of Ser. No. 72,799, Sept. 16, 1970, abandoned.

[51] Int. Cl.$^2$ .................. C07D 487/04; A61K 31/505
[52] U.S. Cl. .................. 424/250; 424/248.56; 544/115; 544/119
[58] Field of Search ........... 260/247.5, 256.4, 256.4 F; 424/248, 250

[56] References Cited

U.S. PATENT DOCUMENTS

3,838,126  9/1974  Wagner .................. 260/256.4

*Primary Examiner*—Henry R. Jiles
*Assistant Examiner*—R. W. Ramsuer
*Attorney, Agent, or Firm*—Gerald D. Sharkin; Richard E. Vila; Joseph J. Borovian

[57] ABSTRACT

The invention discloses 5-substituted-1,2,4-triazolo[4,3-c]quinazolines and 1,2,4-triazolo[1,5-c]quinazolines having pharmacological activity in animals and useful, for example, as hypotensive and anti-inflammatory agents. The compounds may be prepared, for example, by reacting a 5-halo-1,2,4-triazolo-quinazoline with a compound representing the function to be introduced at the 5-position. The 5-halo-1,2,4-triazolo[4,3-c]quinazolines also have pharmacological activity, e.g., hypotensive and anti-inflammatory activity, and may be prepared by reacting a 4-hydrazino-quinazoline with trimethoxy methane. The 5-halo-1,2,4-triazolo[1,5-c]quinazolines also have hypotensive and anti-inflammatory activity and are prepared from the corresponding 1,2,4-triazolo-[1,5-c]quinazolin-5(1H)-one using phosphorus oxychloride, the quinazolin-5(1H)-one being in turn prepared from the 5-halo-1,2,4-triazolo[4,3-c]quinazoline.

28 Claims, No Drawings

TRICYCLIC 1,2,4-TRIAZOLO-QUINAZOLINES

This application is a continuation-in-part of application Ser. No. 339,177, filed Mar. 8, 1973, which in turn is a continuation-in-part of application Ser. No. 209,425, filed Dec. 17, 1971, which in turn is a continuation-in-part of application Ser. No. 72,799, filed Sept. 16, 1970, all of which are now abandoned.

The present invention relates to 5-substituted-1,2,4-triazolo [4,3-c]quinazolines and to 5-substituted-1,2,4-triazolo[1,5-c]quinazolines including the 5-halo substituted compounds which can be used as intermediates in the preparation of other 5-substituted compounds of the present invention. The invention also relates to pharmaceutical compositions and methods utilizing the pharmacological properties of such compounds.

In one major aspect of the present invention, there is provided 1,2,4-triazolo[4,3-c]quinazolines and 1,2,4-triazolo[1,5-c]quinazolines which collectively may be represented by the following structural formula:

I wherein

Q and $R_a$ are different and either a nitrogen atom or a =CR'''-function,

R° represents -OR or

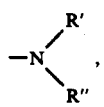

and

R represents lower alkyl of 1 to 6 carbon atoms; allyl; methylallyl, e.g., methallyl; propargyl; di(lower of 1 to 3 carbon atoms)alkylamino (lower of 1 to 4 carbon atoms) alkyl, e.g., dimethylaminopropyl; or —$(CH_2)_m$-$CH(CH_2)_p$ in which m is 0, 1, 2 or 3 and p is 2 to 5;

R' represents hydrogen, and

R'' represents hydrogen; lower alkyl of 1 to 5 carbon atoms; allkyl; methylallyl, propargyl; cycloalkyl of 3 to 6 carbon atoms; or di(lower of 1 to 3 carbon atoms)alkylamino (lower of 1 to 4 carbon atoms) alkyl, e.g., dimethylaminoethyl; or lower alkoxy (of 1 to 4 carbon atoms) lower alkyl (of 1 to 4 carbon atoms); or R' and R'' together with the nitrogen attached to the ring represent di(lower of 1 to 3 carbon atoms)alkylamino; diallylamino; di(methylallyl)amino; or dipropargylamino; or R' and R'' together with the nitrogn attached to the tricyclic ring system form a 3 to 6 membered saturated heterocyclic group represented by:

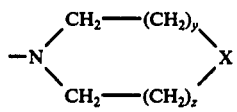

wherein

X is (a) a direct bond, (b) methylene, (c) oxygen or (d) —$N-R_x$ wherein $R_x$ is hydrogen or lower alkyl of 1 to 3 carbon atoms, and y and z are 0 or 1, provided that X is a direct bond when either of y or z is 0, e.g., 4-methylpiperazinyl, R''' represents hydrogen or lower alkyl of 1 to 4 carbon atoms, $R_1$ represents halo of atomic weight of from 19 to 80, lower alkyl of 1 to 3 carbon atoms, lower alkoxy of 1 to 3 carbon atoms, nitro, trifluoromethyl or, when n is 2, the two $R_1$ together form methylenedioxy, and n is 0, 1, 2 or 3, and when 2, then $R_1$ may be the same or different, and when 3, then all $R_1$ are alkoxy; provided that n is 1 when $R_1$ is nitro or trifluoromethyl;

The invention also provided procedures for the production of the compounds of formula I, characterized by A. producing a compound of formula Ia:

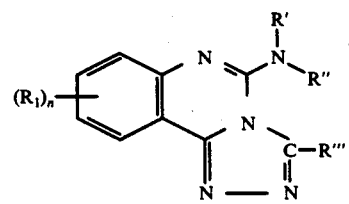
Ia in which $R_1$, n, R', R'' and R''' are as defined above, by reacting a compound of formula II:

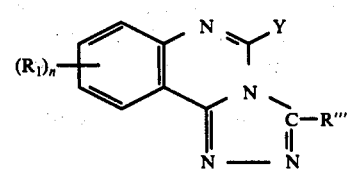
II in which $R_1$, R''' and n are as defined above, and

Y signifies a chlorine or bromine atom, with a compound of formula III:

III in which R' and R'' are as defined above;

B. producing a compound of formula Ib:

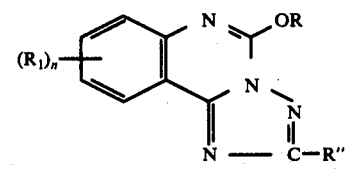
Ib in which $R_1$, n, R and R''' are as defined above, by reacting a compound of formula II, stated above, with a compound of formula IV:

MOR                        IV in which

R is as defined above, and

M signifies a hydrogen atom or an alkali metal or alkaline earth metal cation, the process being carried out in the presence of an inert has base when the compound of formula IV is a free alcohol;

C. producing a compound of formula Ia, stated above, by reacting a compound of formula V:

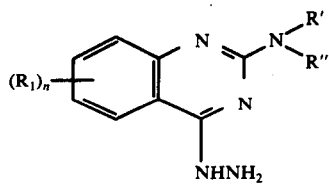

in which $R_1$, $n$, R' and R'' are as defined above, with a compound of formula VI:

in which R''' is as defined and $m$ signifies 0 or 1, under substantially anhydrous conditions;

D. producing a compound of the formula Ic:

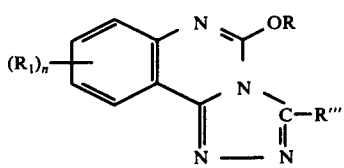

in which $R_1$, $n$, R and R''' are as defined above, by reacting a compound of the formula II, stated above, with an alcohol of the formua IV, stated above, under controlled time and temperature conditions in the presence of an inert base;

E. producing a compound of the formula Id:

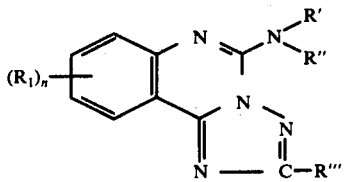

in which $R_1$, $n$, R', R'' and R''' are as above defined, by reacting a compound of the formula VII:

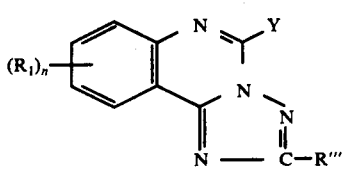

in which $R_1$, $n$, R''' and Y are as defined above, with a compound of the formula III, stated above;

F. producing a compound of the formula Id, stated above, by subjecting a compound of the formula Ia, stated above, to rearrangement under basic conditions;

G. producing a compound of the formula Ib, stated above, by reacting a compound of the formula VII, stated above, with a compound of the formula IV, stated above, with the process being carried out in the presence of an inert base when the compound of the formula IV is a free alcohol;

H. producing a compound of the formula Ib or Id by heating a corresponding compound of the formula Ic or Ia respectively in the presence of a lower carboxylic acid; or I. producing a compound of the formula Ib or Ib by heating a corresponding compound of the formula Ic or Ia respectively above its melting point.

The preparation of compounds Ia by procedure A involving reaction of a compound II with a compound III may be conveniently carried out in a solvent medium at temperatures in the range of 10° to 200° C. In many forms of practice, it is convenient to employ an excess of the compound III as solvent for the reaction. Various of the several wellknown conventional organic solvents may also be employed. Examples of the more suitable conventional solvents include chloroform, methylene chloride, ethanol, benzene, toluene, dioxane and dimethylacetamide. The used of elevated temperatures may beneficially influence reaction rates although the preferred reaction temperatures may depend upon the choice of the reaction solvent.

The preparation of compounds Ib by procedure B involving reaction of a compound II with a compound IV is suitably effected at a temperature of from 10° to 120° C., preferably 15° to 60° C., and in the presence of a solvent. Suitable solvents include inert, non-hydroxylic solvents, and also the alcohols corresponding to the compounds of the formula IV, for example, allyl alcohol when compound IV is an allyloxide. The compound IV is most suitably the sodium salt. When the compound IV is an alcohol, the process is conveniently carried out using an excess thereof to provide a solvent, and for relatively long periods, e.g., about 48 hours, and at a temperature of at least 40° to 50° C., preferably at reflux temperatures. Suitable inert organic bases include triethylamine. When employing inorganic bases the reaction is carried out under anhydrous conditions, the preferred bases being the alkali metal bases such as potassium hydroxide.

The preparation of compounds Ia by procedure C involving reaction of a compound V with a compound V is suitably effected at temperatures of from 10° to 150° C., preferably at about 15° to 50° C. An inert solvent may be employed but the process is suitably effected employing an excess of the compound VI which is preferably the compound VI in which $m$ is 0, e.g., trimethoxy methane. The reaction may be also suitably effected in the presence of an acid, e.g., a strong acid, such as p-toluenesulphonic acid.

The preparation of compounds Ic by procedure D involving reaction of a compound II with the appropriate alcohol of the formula IV (compounds IV in which M is hydrogen) is effected under controlled time and temperature conditions so as to avoid unwanted formation of a compound Ib. In general, the reaction may be carried out suitably at temperatures of from 10° to 60° C. for a period of time varying inversely with the temperature. Preferred conditions involve temperatures between 15° to 50° C. and times between 5 to 30 hours. The preferred inert organic bases include triethylamine and the like. When an inorganic base is employed the reaction is conducted under anhydrous conditions, the preferred bases being the alkali metal bases such as potassium hydroxide.

The preparation of compounds Id by procedure E involving the reaction of a compound of the formula VII with a compound of the formula III is carried out analogously to procedure A.

The preparation of compounds Id by procedure F involves a rearrangement of a compound of the formula Ia and is suitably effected by subjecting the latter to the action of a strong base at temperatures of from 30° to 120° C., preferably 50° to 100° C. The generally preferred bases are the alkali metal alkoxides such as sodium ethoxide. The rearrangement reaction may be carried out in the presence of an inert organic solvent such as a lower alochol, e.g., methanol.

The preparation of compounds Ib by procedure G involving the reaction of a compound VII with a compound IV is suitably carried out analogously to the reaction of procedure B.

The preparation of a compound Ib or Id by procedure H involves heating a corresponding compound of the formula Ic or Ia respectively at temperatures in the range of from 70° to 180° C., preferably 100° to 160° C., in the presence of a lower carboxylic acid, preferably acetic acid, for extended time periods of typically at least 24 hours, preferably at least 36 hours. The reaction may be carried out in the presence of an inert organic solvent which is preferably of the higher boiling type such as an aromatic solvent, e.g., xylene.

The preparation of a compound Ib or Id by procedure I is suitably effected by fusing a corresponding compound of the formula Ic or Ia respectively for moderate time periods of typically at least 1 hour, more usually about 2 to 4 hours.

The various compounds of formula I produced by the reactions of the above-described procedures A-I may be isolated and purified from the various reaction systems in which they are formed by using conventional techniques. Where desired or required, free base forms of the basic compounds of formula I may be converted into acid addition salt forms in conventional manner, and vice versa.

The compounds of formula II are novel compounds and may be provided by reacting a compound of formula VIII:

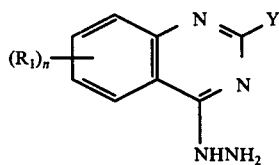

VIII in which $R_1$, $n$ and Y are as defined above, with a compound of formula VI, stated above, under substantially anhydrous conditions. The process may be effected as described above for procedure C. The resulting compounds of formula II may be isolated and purified using conventional techniques.

The compounds of formula VIII, employed in producing compounds of formula II, may be produced by reacting a compound of formula IX:

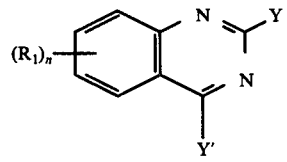

IX in which $R_1$, $n$ and Y are as defined above, and Y' signifies a chlorine or bromine atom, with hydrazine. The process is suitably carried out at a temperature of from 0° to 30° C., preferably 5° to 25° C., and in an inert organic solvent, such as an aromatic solvent, e.g., benzene or toluene, a chlorinated hydrocarbon, e.g., methylene chloride, or a dialkylamide, e.g., dimethylacetamide. The resulting compounds of formula VIII may be isolated and purified using conventional techniques.

The compounds of formula IX are either known or may be produced in conventional manner from available materials, for example, by the procedures of Curd et al., J. Chem. Soc. 1948, 1759 and Hens et al., J. Med. Chem. 11, 130–136 (1968). In the prior art, 2,4-dichloro or dibromo quinazolines are produced by firstly cyclizing an anthranilic acid or ester with an alkali metal cyanate, preferably in acetic acid and at a temperature of from 80° to 120° C., to obtain the corresponding quinazoline-2,4-dione, and then reacting this with phosphorus oxychloride or oxybromide, suitably at a temperature of from 80° to 120° C. It has now been found advantageous to employ the methyl or ethyl ester of anthranillic acid rather than the acid itself.

The compounds of formula V, employed as starting materials in procedure C), may be produced by reacting a compound of formula VIII, stated above, with a compound of formula III, stated above, in a solvent. The process is suitably carried out analogously to procedure A. The compounds V may be recovered from the reaction by conventional procedures.

The compounds of the formula VII employed as starting material in Procedures E and G are preferably prepared by halogenation of a compound of the formula X:

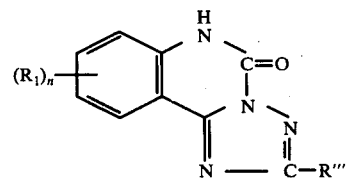

X in which $R_1$, $n$ and R''' are as above defined. The preparation of compounds VII from X may be carried out in a conventional manner for halogenating a cyclic keto function. Preferably the reaction is carried out employing excess phosphorus oxychloride or phosphorus oxybromide as the halogenating agent and solvent for the reaction. Temperature for the reaction may vary fairly widely between 50° to 180° C., although the reaction is preferably conducted at the reflux temperature of the reaction mixture. If desired, a minor amount of a tertiary amine such as dimethylaniline may be employed as a catalyst for the reaction.

The compounds of the formula X are novel and may be prepared by subjecting a compound of the formula II either to the action of a concentrated organic acid followed by hydrolysis or to the action of a strong inorganic base in the presence of water whereby a combined hydrolysis and rearrangement takes place. The reaction of a compound II with an organic acid is effected at temperatures in the range of from 50° to 150° C, preferably 100° to 130° C., and preferably employs an excess of glacial acetic acid which also serves as the solvent for the reaction. The subsequent hydrolysis is readily effected, for example, by contacting the reaction product with water for short periods of time at about room temperature. The preparation of compounds X from compounds II in the presence of a base is suitably carried out at temperatures in the range of from 60° to 120° C., preferably 80° to 110° C. The more preferred strong bases include the alkali metal hydroxides, e.g. potassium hydroxide. The reaction is carried out in a liquid medium which is preferably water such that a preferred system for effecting the hydrolysis-rearrangement will constitute, for example, a 10% aqueous solution of potassium hydroxide.

The compounds of the formula III and IV employed in the various reactions described herein are either known or may be prepared from known materials by established procedures.

At the time of our earlier application Ser. No. 72,799 it was believed that the reaction of Procedure B herein resulted in the compounds of the formula Ic herein. Contrary to our earlier belief, it has been now established that the conditions of the said Procedure B result in a splitting and rearrangement of the triazole ring of the nucleus with the result that the compounds of the formula Ib herein are formed Compounds of formula I may form acid addition salts, and may be produced and isolated such as acid addition salts, as desired or required. It will be evident that the non-toxic acid addition salts not materially affecting the pharmacological effect of the compounds I are also within the scope of the present invention. Such pharmaceutically acceptable salts may include, by way of illustration, the hydrochloride, fumarate, maleate, formate, acetate, sulfonate and malonate. The acid addition salts of the subject compounds I may be produced from the corresponding free bases by conventional procedures. Conversely, the free bases may be obtained from the salts by procedures known in the art.

The compounds of structural formulae, I, II and VII and their pharmaceutically acceptable acid addition salts are useful because they possess pharacological activity in animals. In general, the compounds are useful as hypotensive agens, as indicated by a lowering of blood pressure on intravenous administration to the anesthetized dog. For the above use, the compounds may be combined with a pharmaceutically acceptable carrier, and such other conventional adjuvants as may be necessary, and adminstered orally in such forms tablets, capsules, elixirs, suspensions and the like or parenterally in the form of an injectable solution or suspension. For the above-mentioned use, the dosage administered will, or course, vary depending upon the compounds used and the mode of administration. However, in general, satisfactory results are obtained when administered at a daily dosage of from about 2 milligrams to about 50 milligrams per kilogram of body weight, preferably given in divided doses 2 to 4 times a day, or in sustained release form. For most mammals the administration of from about 120 milligrams to about 1000 milligrams of the compound per day provides satisfactory results and dosage forms suitable for internal administration comprise from about 30 milligrams to about 500 milligrams of the compound in admixture with a solid or liquid pharameceutical carrier or diluent. The compounds of the formula I as represented by those of Examples 1 and 2 hereinafter have also been found to exhibit antihypertensive activity as indicated by ability to lower blood pressure in the renal hypertensive rat on oral administration. Such result may be satisfactory obtained upon the administration of a daily dosage of from 3 to 150 milligrams per kilograms of body weight with the daily dose for most mammals being in the range of from 200 milligrams to about 1000 milligrams and divided dosage forms containing from about 50 to 500 milligrams of the compound in admixture with a solid or liquid carrier or diluent.

The compounds of the formulae I, II and VII are also useful as antiinflammatory agents as indicated by the Carrageenan-induced edema test in rats and/or an inhibition of skin lesions provided by Freud's adjuvant in the guinea pig. For such use satisfactory results are obtained on the administration of a daily dose of from about 3 to 200 milligrams per kilogram of body weight, preferably given in divided doses, or in sustained release form. For most mammals the administration of from 200 to 3000 milligrams per day provides satisfactory results and dosage forms comprise from 50 to 1500 milligrams in admixture with a solid or liquid pharmaceutical carrier or diluent.

In addition, the compounds of Examples 1 and 2 are also useful as tranquilizers as indicated by effecting a Central Nervous System depression in behavior tests in mice, by exhibiting an antagonism of amphetamine stimulation in mice and by effecting a neurological deficit in the rotarod test in mice. For this use satisfactory results are obtained on the administration of a daily dose of 5 to 200 milligrams per kilogram of body weight with the daily dose for most mammals being between 300 to 3000 milligrams and dosage forms comprising from 75 to 1500 milligrams.

For above usages, oral administration with carriers may take place in such conventional forms as tablets, dispersible powders, granules, capsules, syrups and elixirs. Such composition may be prepared according to any method known in the art for the manufacture of pharmaceutical compositions, and such compositions may contain one or more conventional adjuvants, such as sweetening agents, flavoring agents, coloring agents and preserving agents, in order to provide an elegant and palatable preparation. Tablets may contain the active ingredient in admixture with conventional pharmaceutical excipients, e.g., inert diluents such as calcium carbonate, sodium carbonate, lactose and talc, granulating and disintegrating agents, e.g., starch and alginic acid, binding agents, e.g. starch, gelatin and acacia, and lubricating agents, e.g., magnesium stearate, stearic acid and talc. The tablets may be uncoated or coated by known techniques to delay disintegration and adsorption in the gastro-intestinal tract and thereby provide a sustained action over a longer period. Similarly, suspensions, syrups and elixirs may contain the active ingredient in admixture with any of the conventional excipients utilized for the preparation of such compositions, e.g., suspending agents (methylcellulose, tragacanth and sodium alginate), wetting agents (lecithin, polyoxyethylene stearate and polyoxyethylene sorbitan monooleate) and preservatives (ethyl-p-hydroxybenzoate). Capsules may contain the active ingredient along or admixed with an inert solid diluent, e.g., calcium carbonate, calcium phosphate and kaolin. The preferred pharmaceutical compositions from the standpoint of preparation and ease of administration are solid compositions, particularly hardfilled capsules and tablets.

A representative formulation is a tablet prepared by conventional tabletting techniques and containing the following ingredients:

| Ingredients | Weight (mg.) |
| --- | --- |
| 5-Allyloxy-8,9-dimethoxy-1,2,4-triazolo[1,5-c]quinazoline | 50 |
| Tragacanth | 10 |
| Lactose | 197.5 |
| Corn starch | 25 |
| Talcum | 15 |
| Magnesium stearate | 2.5 |

Preferred compounds from the standpoint of anti-inflammatory activity are of the formula Id1:

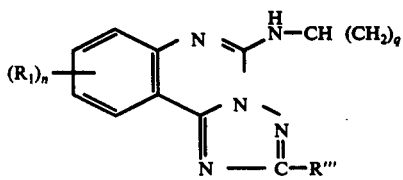

in which $R_1$, $n$ and $R'''$ are as defined and $q$ is 2 to 5. The more preferred such compounds of the formula Id1 have the formula Id2:

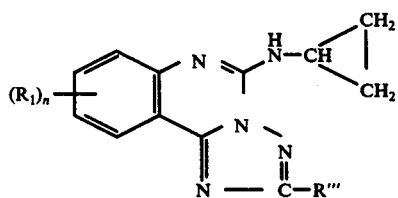

in which $R_1$, $n$ and $R'''$ are as defined. In the compounds of the formulae Id1 and Id2 there is also contemplated a preferenc for the situations in which $(R_1)_n$- is 8,9-dialkoxy, particularly 8,9-dimethoxy.

Another representative formulation for use in the treatment of inflammation on oral administration 2 to 4 times a day is a capsule prepared by conventional tecniques and containing:

| Ingredient | Weight(mg.) |
| --- | --- |
| 5-cyclopropylamino-8,9-dimethoxy-2-methyl-triazolo[1,5-c]quinazoline | 75 |
| Kaolin | 225 |

It has also been found that compounds of the formula Ia1:

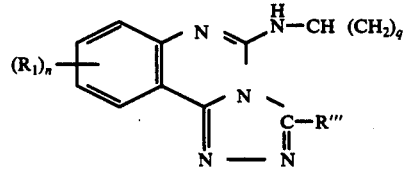

wherein $R_1$, $R'''$, $n$ and $q$ are as above defined, also possess anti-viral activity. In particular, they possess activity against pox viruses, such as Vaccinia Estree, Rabbittpox, Cowpow an Vaccinia WR, as indicated in the plaque reduction test on chicken fibroblasts at a concentration of about 0.01 to 10 μg/ml, and in vivo tests in mice infected with the virus and administered 100 mg/kg of the test compound intraperitoneally.

The compounds are therefore useful fortreating conditions resulting from pox viruses, including corresponding prophylactic use. For this use, the dosage administered will, of course, vary depending on the compound employed, mode of administration and treatment desired. However, in general, satisfactory results are obtained when administered at a daily dosage of from about 30 to 200 mg/kg of animal body weight, conveniently given in divided dosages 2 to 4 times a day, or in sustained release form. For larger mammals, the total daily dosage is in the range of from about 2 to 10 g, and dosage forms suitable for oral administration comprise from about 0.5 to 5 g. of the compound admixed with a solid or liquid pharmaceutical carrier or diluent.

The above-mentioned compounds of the formula Ia1 are also active against Herpes Simplex virus as indicateed in mice. Three groups of twenty mice are injected with the $LD_{50}$ of the Herpes Simplex virus intraperitoneally. The first and second groups are simultaneously administered, intracerebrally, 2.4 mg/kg of, respectively, a standard; namely, cytosine arabinoside (Ara-C) and the test compound. The third group is left untreated (control). The animals are then observed for 13 days, at the end of which the survival rates in the three groups of animals are compared.

The compounds of the formula Ia1 are therefore useful in treating conditions associated with the Herpes Simplex virus. For this use, the dosage administered will, of course, vary depending on the compound administered, mode of administration and treatment desired. However, in general, satisfactory results are obtained when administered at a daily dosage of from 2 to 50 mg/kg of animal body weight, suitably given in divided dosages two to four times daily. For the larger mammals, the total daily dosage is in the range of from about 40 to 1750 mg of the compound in admixture with a liquid pharmaceutical diluent.

A capsule containing 500 milligrams of a compound of formula Ia1, e.g., 5-cyclobutylamino-8,9-dimethoxy-1,2,4-triazolo[4,3-c]quinazoline, is representative of a formulation useful on administration 4 times a day in the treatment of pox virus. A sterile aqueous suspension formulated according to conventional techniques and containing 50 milligrams of a compound of formula Ia1, e.g., 5-cyclobutylamino-8,9-dimethoxy-1,2,4-triazolo[4,3-c]quinazoline, is representative of a dosage form for injection 4 times a day in the treatment of Herpes Simplex virus conditions.

A major class of compounds of the present invention as disclosed in my prior application Serial No. 209,425 are those of the formula I hereinwhich R is other than cycloalkyl or cycloalkylalkyl and R" is other than alkoxyalkyl.

The following examples are merely illustrative of specific compounds of the invention and the manner in which they may be prepared.

EXAMPLE 1

5-Allyloxy-8,9-dimethoxy-1,2,4-triazolo[1,5-c]quinazoline.

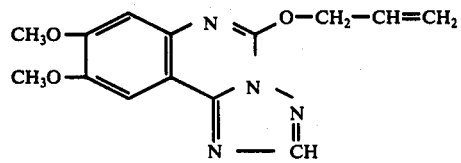

STEP A

Preparation of 6,7-dimethoxy-2-chloro-4-hydrazinoquinazoline.

To a solution of 20.8 g. of 2,4-dichloro-6,7-dimethoxyquinazoline in 400 ml. of methylene chloride is added dropwise 20 g. of hydrazine while maintaining the temperature below 30° C. with cooling. The resulting mixture was stirred for 45 minutes and then allowed to stand overnight at a temperature of 0° C. The mixture is then filtered and the solids washed first with water and then with methanol. The resulting solid material is then taken up in ice-water and stirred for 20 minutes. The mixture is then filtered and the resulting solid is recrystallized from methanol/methylene chloride to obtain 6,7-dimethoxy-2-chloro-4-hydrazino-quinazoline, m.p. 312°-315° C. (decomp.).

STEP B:

Preparation of 5-chloro-8,9-dimethoxy-1,2,4-triazolo [4,3-c]quinzoline.

A mixture of 10.0 g. of 6,7-dimethoxy-2-chloro-4-hydrazinoquinazoline, 1.0 g. of p-toluenesulfonic acid and 150 ml. of trimethoxy methane is refluxed with stirring for 19 hours and then stirred for 24 hours at room temperature. The resulting mixture is evaporated in vacuo to dryness and the residue dissolved in 1500 ml. of methylene chloride. This solution is extracted twice with sodium carbonate solution, washed neutral with water, dried and evaporated in vacuo to dryness. The residue is twice crystallized from methylene chloride/ diethyl ether and then from ethanol to obtain 5-chloro-8,9-dimethoxy-1,2,4-triazolo[4,3-c]quinazoline, m.p. 269°-271° C.

STEP C

Preparation of 5-allyloxy-8,9-dimethoxy-1,2,4-triazolo[1,5-c]quinazoline.

To 65 ml. of allyl alcohol cooled to room temperature is added 2.8 g. of sodiuom followed by addition of an additional 120 ml. of allyl alcohol. To the resulting mixture at room temperature is added 15.0 g. of 5-chloro-8,9-dimethoxy-1,2,4-triazolo[4,3-c]quinazoline. The resulting precipitate is filtered off, washed with diethyl ether, dissolved in methylene chloride, washed with water, dried and evaporated in vacuo to dryness. The residue is twice crystallized from ethanol after treatment with charcoal to obtain 5-allyloxy-8,9-dimethoxy-1,2,4-triazolo[1,5-c]quinazoline, m.p. 189°-191° C.

EXAMPLE 2

5-Morpholino-8,9-dimethoxy-1,2,4-triazolo[4,3-c]quinazoline.

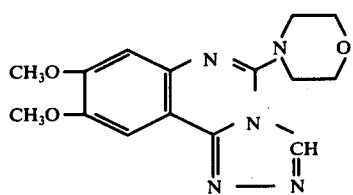

A mixture of 10.0 g. of 5-chloro-8,9-dimethoxy-1,2,4-triazolo[4,3-c]quinazoline, 38.8 g. of morpholine and 100 ml. of ethanol is refluxed for 1.5 hours and the resulting mixture evaporated in vacuo to dryness. The residue is taken up with ethanol and diethyl ether and filtered. The resulting solid is then recrystallized from benzene, filtered, washed with diethyl ether, recrystallized from ethanol and dried in a high vacuum to obtain 5-morpholino-8,9-dimethoxy-1,2,4-triazolo[4,3-c]quinazoline, m.p. 216°-218° C.

EXAMPLE 3

Following essentially the procedure of Examples 1 and 2 the following compounds of the invention are prepared:
a. 5-[2-(dimethylamino)ethylamino]-8,9-dimethoxy-1,2,4-triazolo[4,3-c]quinazoline, m.p. 212°-214° C. (Crystallized from benzene and washed with diethyl ether).
b. 5-ethoxy-8,9-dimethoxy-1,2,4-triazolo[1,5-c]quinazoline.
c. 5-[2-(diethylamino)ethoxy]-8,9-dimethoxy-1,2,4-triazolo [1,5-c]quinazoline, m.p. 159°-160° C.
d. 5-(4-methylpiperazino)-8,9-dimethoxy-1,2,4-triazolo [4,3-c]quinazoline.
e. 5-methoxy-1,2,4-triazolo[1,5-c]quinazoline, m.p. 163°-164° C.
f. 5-(4-methylpiperazino)-1,2,4-triazolo[4,3-c]quinazoline, m.p. 182°-183° C.
g. 5-cyclopropylamino-8,9-dimethoxy-1,2,4-triazolo[4,3-c]quinazoline, m.p. 250°-251° C.
h. 5-aziridino-8,9-dimethoxy-1,2,4-triazolo[4,3-c]quinazoline, m.p. 160° C. (dec.).
i. 5,8,9-trimethoxy-1,2,4-triazolo[1,5-c]quinazoline, m.p. 228°-230° C.
j. 5-[3-(diethylamino)propoxy]-8,9-dimethoxy-1,2,4-triazolo[1,5-c]quinazoline, m.p. 128°-130° C.

EXAMPLE 4

5-(4-Methylpiperazino)8,9-Dimethoxy-1,2,4-triazolo-[1,5-c]quinazoline

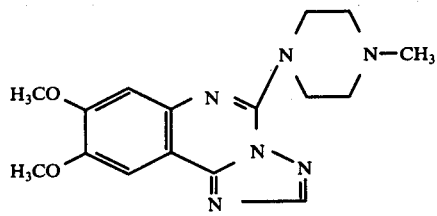

10.1 g of 5-(4-methylpiperazino)-8,9-dimethoxy-1,2,4-triazolo-[4,3-c]quinozoline is refluxed with 2 gms sodiummethoxide in 600 ml methanol for 90 minutes. The mixture is evaporated in vacuo to dryness, treated with water and extracted several times with methylene chloride. The combined methylene chloride extracts after washing with water, are dried and evaporated in vacuo. The residue is dessolved in minimum chloroform and chromotographed on silica gel, the elution being carried out first with chloroform and then with chloroform with increasing concentrations of methanol. The desired fractions, after evaporation in vacuo and crystallization from methylene chloride/diethyl ether gave 5-(4-methylpiperazino)-8,9-dimethoxy-1,2,4-triazolo-[1,5-c]-quinazoline, m.p. 194°-196° C.

EXAMPLE 5

5,8,9-Trimethoxy-1,2,4-triazolo-[4,3-c]quinazoline

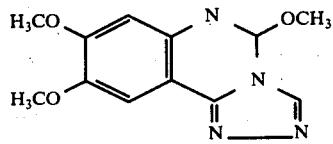

A mixture of 500 mg 5-chloro-8,9-dimethoxy-1,2,4-triazolo[4,3-c]quinazoline and 25 ml triethylamine in 25 ml. methanol is stirred at 40° C. for 24 hrs. The solution is then evaporated in vacuo to dryness, treated with water, and the aqueous layer extracted several times with chloroform. The combined chloroform extracts, after washing with H₂O, is dried over sodium sulfate and evaporated in vacuo to dryness. The residue is dissolved in minimum chloroform and chromotrographed on silica gel, elution being carried out with chloroform and then with chloroform containing increasing concentration of methanol. The desired fractions are collected, evaporated to dryness in vacuo and the residue crystallized from methylene chloride/diethyl ether to obtain 5,8,9-Trimethoxy-1,2,4-triazolo-[4,3-c]quinazoline, m.p. 245°-250° C.

EXAMPLE 6

Preparation of 5-chloro-8,9-dimethoxy-1,2,4-triazolo[1,5-c]-quinazoline.

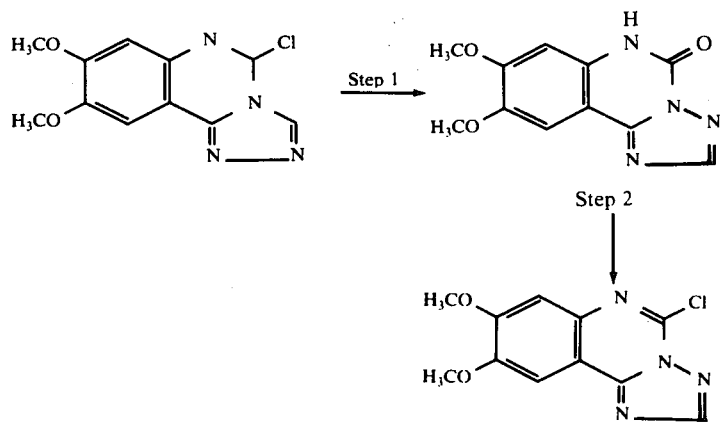

Step 1

8,9-Dimethoxy-1,2,4-triazolo-[1,5-c]quinazoline-5-one 500 mg of 5-chloro-8,9-Dimethoxy-1,2,4-triazolo-[4,3-c]quinazoline is refluxed with 50 ml glacial acetic acid for 1 hour. The mixture is then evaporated in vacuo to dryness. The residue is treated with water/methylene chloride/diethyl ether and the solid material which is, 8,9-Dimethoxy-1,2,4-triazolo-[1,5-c]quinazoline-5-one is filtered off, washed well with water, then diethyl ether and dried, m.p. 320°-325° C.

Step 2.

5-chloro-8,9-dimethoxy-1,2,4-triazolo-[1,5-c]-quinazoline 300 mg of 8,9-Dimethoxy-1,2,4-triazolo-[1,5-c]quinazoline-5-one is refluxed with 5 ml Phosphorous oxychloride and a catalytic amount of N,N-dimethylamline for 18 hours. The reaction mixture is then evaporated in vacuo to dryness; the residue taken up in methylene chloride and the methylene chloride layer extracted several times with cold sodium bicarbonate solution, with water, dried and then avaporated in vacuo to dryness. The residue is crystallized from methylene chloride/diethyl ether to give 5-chloro-8,9-dimethoxy-1,2,4-triazolo-[1,5-c]-quinazoline, m.p. 258°-260°.

EXAMPLE 6A

Following the procedure of Example 6 the following compounds are prepared:
A. 1,2,4-triazolo[1,5-c]quinazoline-5-one, m.p. 310-314° C.
B. 5-chloro-1,2,4-triazolo[1,5-c]quinazoline.

EXAMPLE 7

Following the procedure of Example 2 except that 5-chloro-8,9-dimethoxy-1,2,4-triazolo[1,5-c]quinazoline is used in place of the 5-chloro-8,9-dimethoxy-1,2,4-triazolo[4,3-c]quinazoline, the following compounds of the invention are prepared.
a. 5-(4-methylpiperazino)-8,9-dimethoxy-1,2,4-triazolo[1,5-c]quinazoline, m.p. 194-195° C.
b. 5-cyclopropylamine-8,9-dimethoxy-1,2,4-triazolo[1,5-c]quinazoline, m.p. 209° C.

EXAMPLE 7A

Following the general procedure of Example 7 there is also produced:
a. 5-(4-methylpiperazino)-1,2,4-triazolo[1,5-c]quinazoline, m.p. 131°-133° C.

EXAMPLE 8

Following the procedure of Example 5 the following compounds of the invention are obtained:
a. 5-methoxy-1,2,4-triazolo[4,3-c]quinazoline, m.p. 172°-175° C.
b. 5-allyloxy-8,9-dimethoxy-1,2,4-triazolo[4,3-c]quinazoline, m.p. 171°-173° C.

EXAMPLE 9

The following NMR data provides further characterizations of illustrated compounds of the invention and also support for conclusions as to structure of the various compounds of the invention. The NMR data (on Varian A-60 or T-60) reports chemical shifts for CDCl₃ solutions in ppm., with TMS as the internal standard.

NMR DATA

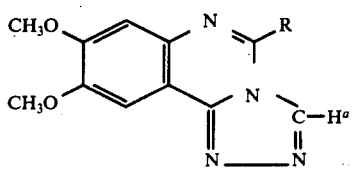 

| Ex. No. | R | $S_H{}^a$ | Ex. No. | R | $S_H{}^b$ |
|---|---|---|---|---|---|
| — | H | 8.83 | — | H | 8.40 |
| 1-B | Chloro | 8.91 | 6 | Chloro | 8.34 |
| 5 | —OCH₃ | 8.80 | 3i | —OCH₃ | 8.38 |
| 3d | 4-methylpiperazino | 8.80 | 4 | 4-methylpiperazino | 8.29 |
| 2 | morpholino | 8.85 | 3b | —OCH₂CH₃ | 8.38 |
| 3a | dimethylaminoethylamino | 9.05 | 1 | —OCH₂CH=CH₂ | 8.30 |
|   |   |   | 3c | diethylaminoethoxy | 8.35 |
|   |   |   | 3j | diethylaminopropoxy | 8.35 |

EXAMPLE 10

Further following the procedure of Example 2 except that an appropriately substituted or unsubstituted 5-chloro-1,2,4-triazolo[1,5-c] quinazoline is used in place of the 5-chloro-8,9-dimethoxy-1,2,4-triazolo [4,3-c]quinazoline, the following additional compounds of the invention are prepared:

a. 5-cyclopentylamino-8,9-dimethoxy-1,2,4-triazolo[1,5-c] quinazoline, m.p. 153°-154° C.
b. 5-cyclobutylamino-8,9-dimethoxy-1,2,4-triazolo[1,5-c] quinazoline, m.p. 166°-168° C.
c. 5-cyclopropylamino-2-methyl-8,9-dimethoxy-1,2,4-triazolo[1,5-c]quinazoline, m.p. 186°-187° C.
d. 5-cyclohexylamino-8,9-dimethoxy-1,2,4-triazolo[1,5-c] quinazoline, m.p. 184°-185° C.
e. 5-aziridino-8,9-dimethoxy-1,2,4-triazolo[1,5-c] quinazoline, m.p. 186°-190° C.
f. 5-(2-methoxyethyl)amino-8,9-dimethoxy-1,2,4-triazolo[1,5-c]quinazoline, m.p. 143°-144° C.
g. 5-cyclopropylamino-1,2,4-triazolo[1,5-c]quinazoline, m.p. 135°-137° C.
h. 5-cyclopropylamino-2-ethyl-8,9-dimethoxy-1,2,4-triazolo [1,5-c]quinazoline, m.p. 173°-175° C.
i. 5-cyclopropylamino-2-isopropyl-8,9-dimethoxy-1,2,4-triazolo[1,5-c]quinazoline.
j. 5-cyclopropylamino-2-n-propyl-8,9-dimethoxy-1,2,4-triazolo[1,5-c]quinazoline.
k. 5-cyclopropylamino-2-n-butyl-8,9-dimethoxy-1,2,4-triazolo[1,5-c]quinazoline.
l. 5-cyclopropylamino-2-methyl-9-chloro-1,2,4-triazolo [1,5-c]quinazoline.
m. 5-cyclopropylamino-2-ethyl-9-chloro-1,2,4-triazolo [1,5-c]quinazoline.
n. 5-cyclopropylamino-2-methyl-9-methoxy-1,2,4-triazolo [1,5-c]quinazoline.
o. 5-cyclopropylamino-2-methyl-9-nitro-1,2,4-triazolo [1,5-c]quinazoline.
p. 5-cyclopropylamino-2-methyl-8,9-dimethyl-1,2,4-triazolo [1,5-c]quinazoline.
q. 5-isopropylamino-2-methyl-8,9-dimethoxy-1,2,4-triazolo [1,5-c]quinazoline.

EXAMPLE 11

Following the procedure of Steps A and B of Example 1, there is prepared 5-chloro-8,9-dimethoxy-3-methyl-1,2,4-triazolo[4,3-c] quinazoline, m.p. 269°-270° C.

EXAMPLE 12

Further following the procedure of Example 1 or Example 2, the following additional compounds of the invention are prepared:

a. 5-cyclohexylamino-8,9-dimethoxy-triazolo[4,3-c]quinazoline, m.p. 210°-212° C.
b. 5-cyclopentylamino-8,9-dimethoxy-triazolo[4,3-c]quinazoline, m.p. 213°-214° C.
c. 5-cyclobutylamino-8,9-dimethoxy-triazolo[4,3-c]quinazoline, m.p. 235°-237° C.
d. 5-cyclopropylamino-3-methyl-8,9-dimethoxy-triazolo[4,3-c] quinazoline, m.p. 214°-215° C.
e. 5-cyclopropylamino-3-ethyl-8,9-dimethoxy-triazolo[4,3-c] quinazoline, m.p. 164°-165° C.
f. 5-cyclopropylmethoxy-8,9-dimethoxy-1,2,4-triazolo[1,5-c] quinazoline, m.p. 220°-221° C.
g. 5-cyclopentyloxy-8,9-dimethoxy-1,2,4-triazolo[1,5-c] quinazoline, m.p. 189°-190° C.

What is claimed is:
1. A compound of the formula

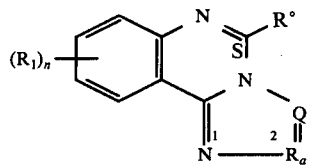

wherein
Q and $R_a$ are different and either a nitrogen atom or a =CR'''-function,
R° represents

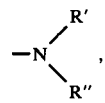

R' represents hydrogen, and
R" represents hydrogen; lower alkyl of 1 to 5 carbon atoms; allyl; methylallyl; propargyl; cycloalkyl of 3 to 6 carbon atoms; or di(lower of 1 to 3 carbon atoms)alkylamino(lower of 1 to 4 carbon atoms)alkyl; or lower alkoxy of 1 to 4 carbon atoms (lower of 1 to 4 carbon atoms)alkyl; or
R' and R" together with the nitrogen attached to the ring represent di(lower of 1 to 3 carbon atoms)alkylamino; diallylamino; di(methylallyl)amino; or dipropargylamino; or R' and R" together with the nitrogen attached to the tricyclic ring system form a 3 to 6 membered saturated heterocyclic group represented by:

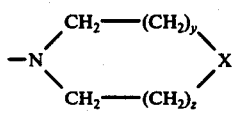

wherein X is (a) direct bond or (b) methylene, and y and z are 0 or 1, provided that X is a direct bond when either y or z is 0;

R''' represents hydrogen or lower alkyl of 1 to 4 carbon atoms;

$R_1$ represents fluoro, chloro, bromo, lower alkyl of 1 to 3 carbon atoms, lower alkoxy of 1 to 3 carbon atoms, nitro, trifluoromethyl or, when n 2, the two $R_1$'s together form methylenedioxy, and n is 0, 1, 2 or 3, and when 2, then $R_1$ may be the same or different, and when 3, then all $R_1$'s are alkoxy; provided that n is 1 when $R_1$ is nitro or trifluoromethyl.

2. A compound of claim 1 having the formula:

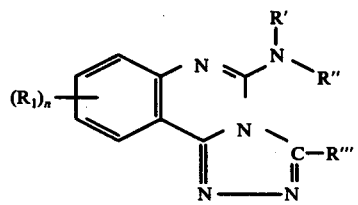

wherein R', R", R''', $R_1$ and n are as defined in claim 1.

3. A compound of claim 2 in which R' and R" together with the nitrogen atom attached to the tricyclic ring system form

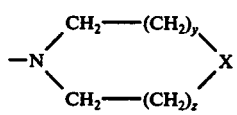

4. A compound of claim 3 in which each of y and z are 1.

5. A compound of claim 1 having the formula:

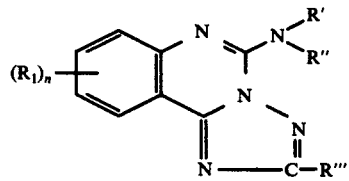

wherein $R_1$, n, R', R" and R''' are as defined in claim 1.

6. A compound of claim 5 in which R' and R" together with the nitrogen atom attached to the tricyclic ring system form

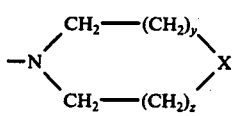

7. A compound of claim 6 in which each of y and z are 1.

8. A compound of claim 5 having the formula:

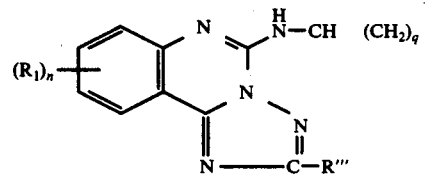

in which q is 2 to 5.

9. A compound of claim 8 having the fomrula:

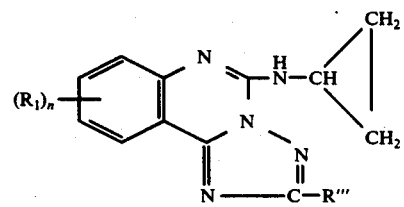

10. A compound of claim 9 in which $(R_1)_n$- is 8,9-dimethoxy.

11. The compound of claim 10 in which R''' is hydrogen.

12. The compound of claim 10 in which R''' is methyl.

13. The compound of claim 10 in which R''' is ethyl.

14. The compound of claim 10 in which R''' is isopropyl.

15. A compound of claim 8 in which $(R_1)_n$- is 8,9-dimethoxy.

16. The compound of claim 15 in which R''' is hydrogen and q is 3.

17. A compound of claim 9 in which R''' is methyl.

18. A compound of claim 5 in which R" is lower alkyl.

19. A compound of claim 18 in which $(R_1)_n$- is 8,9-dimethoxy.

20. A compound of claim 1 having the formula

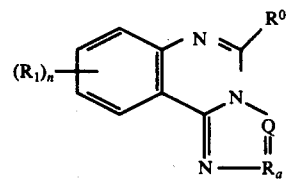

wherein

Q and $R_a$ are different and either a nitrogen atom or a =CR'''-function,

R° represents

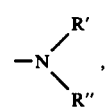

R' represents hydrogen, and

R" represents hydrogen; lower alkyl of 1 to 5 carbon atoms; allyl; methylallyl; propargyl; cycloalkyl of 3 to 6 carbon atoms; or di(lower of 1 to 3 carbon atoms)alkylamino(lower of 1 to 4 carbon atoms)alkyl; or R' and R" together with the nitrogen attached to the ring represent di(lower of 1 to 3 carbon atoms)

alkylamino; diallylamino; di(methylallyl)amino; or dipropargylamino; or

R' and R" together with the nitrogen attached to the tricyclic ring system form a 3 to 6 membered saturated heterocyclic group represented by:

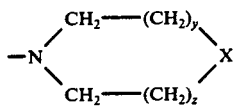

wherein X is (a) a direct bond or (b) methylene, and $y$ and $z$ are 0 or 1, provided that X is a direct bond when either $y$ or $z$ is 0;

R''' represents hydrogen or lower alkyl of 1 to 4 carbon atoms;

$R_1$ represents fluoro, chloro, bromo, lower alkyl of 1 to 3 carbon atoms, lower alkoxy of 1 to 3 carbon atoms, nitro, trifluoromethyl or, when $n$ is 2, the two $R_1$'s together form methylenedioxy, and $n$ is 0, 1, 2 and 3, and when 2, then $R_1$ may be the same or different, and when 3, then all $R_1$'s are alkoxy; provided that $n$ is 1 when $R_1$ is nitro or trifluoromethyl.

21. The compound of claim 2 which is 5-cyclobutylamino-8,9-dimethoxy-1,2,4-triazolo[4,3-c]quinazoline.

22. The compound of claim 2 which is 5-cyclohexylamino-8,9-dimethoxy-1,2,4-triazolo[4,3-c]quinazoline.

23. The compound of claim 2 which is 5-cyclopentylamino-8,9-dimethoxy-1,2,4-triazolo[4,3-c]quinazoline.

24. The compound of claim 2 which is 5-cyclopropylamino-8,9-dimethoxy-1,2,4-triazolo[4,3-c]quinazoline.

25. The compound of claim 2 which is 5-cyclopropylamino-3-methyl-8,9-dimethoxy-1,2,4-triazolo[4,3-c]quinazoline.

26. The compound of claim 2 which is 5-cyclopropylamino-3-ethyl-8,9-dimetoxy-1,2,4-triazolo[4,3-c]quinazoline.

27. A pharmaceutical composition for treating inflammation in mammals comprising an inert pharmaceutically acceptable carrier and an anti-inflammatory effective amount of a compound of claim 20.

28. A method of treating inflammation in mammals comprising administering to a mammal in need of such treatment an anti-inflammatory effective amount of a compound of claim 20.

* * * * *